United States Patent
Benfeldt et al.

(10) Patent No.: US 9,629,388 B2
(45) Date of Patent: *Apr. 25, 2017

(54) STRAINS OF PROPIONIBACTERIUM

(71) Applicant: DuPont Nutrition Biosciences ApS, Copenhagen K (DK)

(72) Inventors: Connie Benfeldt, Beder (DK); Heike Ursula Morgenstern, Rønde (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/402,636

(22) PCT Filed: May 21, 2013

(86) PCT No.: PCT/EP2013/060371
§ 371 (c)(1),
(2) Date: Nov. 20, 2014

(87) PCT Pub. No.: WO2013/174793
PCT Pub. Date: Nov. 28, 2013

(65) Prior Publication Data
US 2015/0150298 A1    Jun. 4, 2015

Related U.S. Application Data

(60) Provisional application No. 61/649,691, filed on May 21, 2012, provisional application No. 61/766,952, filed on Feb. 20, 2013.

(30) Foreign Application Priority Data

May 21, 2012 (EP) .................................. 12168740
May 17, 2013 (EP) .................................. 13168162

(51) Int. Cl.
| | | |
|---|---|---|
| C12R 1/00 | (2006.01) | |
| A23L 3/3571 | (2006.01) | |
| A23C 9/127 | (2006.01) | |
| A01N 63/00 | (2006.01) | |
| A23L 3/3463 | (2006.01) | |
| C12R 1/01 | (2006.01) | |
| A23K 10/18 | (2016.01) | |
| A23K 30/00 | (2016.01) | |

(52) U.S. Cl.
CPC ............ *A23L 3/3571* (2013.01); *A01N 63/00* (2013.01); *A23C 9/127* (2013.01); *A23K 10/18* (2016.05); *A23K 30/00* (2016.05); *A23L 3/34635* (2013.01); *C12R 1/01* (2013.01); *A23V 2002/00* (2013.01); *A23Y 2220/63* (2013.01); *A23Y 2220/67* (2013.01); *A23Y 2220/73* (2013.01); *A23Y 2320/00* (2013.01); *A23Y 2320/15* (2013.01); *A23Y 2320/25* (2013.01); *A23Y 2320/39* (2013.01)

(58) Field of Classification Search
CPC .............. C12R 1/00; C12R 1/01; C12R 1/225
See application file for complete search history.

(56) References Cited

U.S. PATENT DOCUMENTS

| | | | |
|---|---|---|---|
| 4,728,518 A | 3/1988 | Gonzalez et al. | |
| 5,096,716 A | 3/1992 | Deters et al. | |
| 5,096,718 A | 3/1992 | Ayres et al. | |
| 2005/0153018 A1* | 7/2005 | Ubbink .................. | A23K 1/002 426/61 |

FOREIGN PATENT DOCUMENTS

| | | |
|---|---|---|
| CN | 1708316 A | 12/2005 |
| DE | 202006014937 U1 | 11/2006 |
| EP | 0576780 A2 | 1/1994 |
| EP | 1308506 A1 | 5/2003 |
| EP | 1625795 A1 | 2/2006 |
| WO | 9816124 A1 | 4/1998 |
| WO | 03040349 A1 | 5/2003 |
| WO | 2004041305 A1 | 5/2004 |

OTHER PUBLICATIONS

U.S. Appl. No. 14/402,625.*
International Search Report and Written Opinion of the International Searching Authority of PCT/EP2013/060371, mailed Aug. 23, 2013 (Aug. 23, 2013), the whole document.
Susanne Miescher: "Antimicrobial and Autolytic Systems of dairy Propionibacteria", Dissertation Submitted to the Swiss Federal Institute Oftechnology Zurich for the Degree of Doctor of Technical Sciences, XX, XX, Jan. 1, 1999 (Jan. 1, 1999), pp. 58-62,79, XP002192334, the whole document.
Tawfik, et al., "Preserving Domiati Cheese Using Metabolites of Propionibacterium Thoenii P-127", Polish Journal of Food and Nutrition Sciences, 2004, vol. 13/54, No. 3, pp. 259-272.
Translation of Office Action received for Corresponding Chinese Patent Application No. 201380032552.4, dated Nov. 19, 2015.

* cited by examiner

*Primary Examiner* — Ruth Davis

(57) ABSTRACT

The present invention relates to novel strains of *Propionibacterium* as well as preparations and compositions, such as fermentation broths, protective cultures, final food or feed product with *Propionibacterium* alone or in combination with bacteria of the genus *Lactobacillus*. The present invention further relates to methods for the controlling of growth of a contaminant, such as a bacteria, yeast or mold by using these novel strains of *Propionibacterium*.

7 Claims, 6 Drawing Sheets

STRAINS OF PROPIONIBACTERIUM

CLAIM FOR PRIORITY

Figure 1:
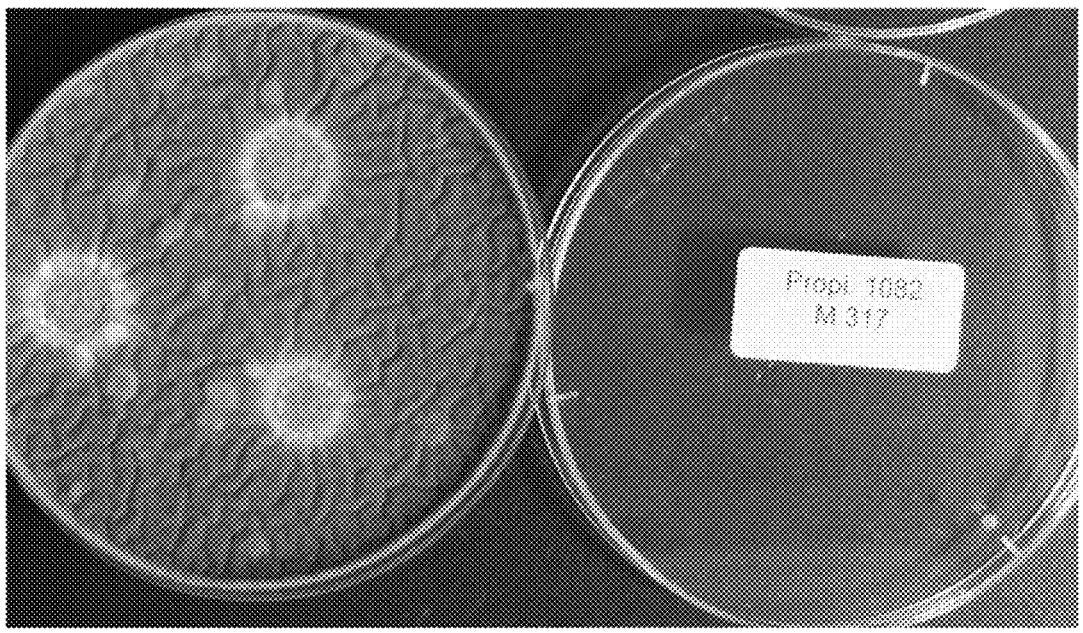

This application claims priority under 35 USC 371 to International Application No. PCT/EP2013/060371, filed on May 21, 2013, which claims priority from U.S. Provisional Patent Application No. 61/649,691, filed May 21, 2012; European Patent Application No. 12168740.4, filed May 21, 2012; U.S. Provisional Patent application No. 61/766,952, filed Feb. 20, 2013; and European Patent Application No. 13168162.9, filed May 17, 2013, each of which is hereby incorporated by reference in its entirety.

FIELD OF THE INVENTION

The present invention relates to novel strains of *Propionibacterium* as well as preparations and compositions, such as fermentation broths, protective cultures, final food or feed products with *Propionibacterium* alone or in combination with bacteria of the genus *Lactobacillus*. The present invention further relates to methods for the controlling of growth of a contaminant, such as a bacteria, yeast or mould by using these novel strains of *Propionibacterium*.

BACKGROUND OF THE INVENTION

Yeasts and moulds play a major role in spoilage of different types of dairy products, like yogurt, sweetened and sour cream and fresh and ripened cheese types and thus can lead to high economic losses. Chemical preservatives like organic acids and their salts (e.g. sorbate and propionate) are used to preserve dairy products and protect and prolong the shelf life. Drawbacks in using chemical preservatives are the labelling requirements (often as E numbers) and potential adverse effects on the sensory properties of the foodstuff.

In 1993 Valio, a finish dairy company described in EP 0576780 the use of a protective culture to inhibit fungal growth. The culture is a mixture of a *Lactobacillus rhamnosus* strain (deposited at Deutsche Sammlung von Mikroorganismen and Zellkulturen GmbH (DSM) with the deposition number DSM 7061) and a *Propionibacterium freudenreichii* subsp. *shermanii* strain (DSM 7067). The specific characteristic of this co-culture was that the combination of the *Lactobacillus* and the *Propionibacterium* had better antifungal activity than the *Lactobacillus rhamnosus* alone. The culture was commercialized by Wiesby under the name "Bio Profit" and renamed into HOLDBAC™ YM-B by Danisco.

EP 0576780 relates to a novel microorganism strain *Lactobacillus casei* ssp. *rhamnosus* LC-705, DSM 7061, having a yeast and mould controlling effect, to bacterial preparation comprising this strain, alone or in combination with a bacterium of the genus *Propionibacterium* or another strain of the bacterium *Lactobacillus casei* and/or with conventional agents used for yeast and mould control.

EP1308506 (Swiss Federal Institute of Technology (ETH) in Zürich, Switzerland) also describes the combination of *lactobacilli* and *propionibacteria*. A *Lactobacillus paracasei* subsp. *paracasei* strain (DSM 14514) from the ETH was commercialized as a blend with *Propionibacterium freudenreichii* subsp. *shermanii* DSM 7067 from Valio under the name HOLDBAC™ YM-C.

Patent WO 03/040349 relates to a mixture of bacteria being a non starter culture which is free from metabolites and comprising the species *Propionibacterium jensenii* and a second bacterium selected from the genus *Lactobacillus*.

U.S. Pat. No. 4,728,516 relates to a method of inhibiting mould and psychrotrophic bacteria in creamed Cottage cheese using a mixture of *Streptococcus lactis* subspecies *diacetylactis* and *Propionibacterium shermanii* in the cream dressing or creamed Cottage cheese at refrigeration temperatures.

DE202006014937 relates to butterfat mixture with reduced fat content, comprises a butter and bio-protective cultures from lactic acid bacteria in the absence of preservatives.

U.S. Pat. No. 5,096,718A relates to metabolite material of *propionibacteria* as well as uses thereof for inhibiting the growth of gram negative psychrotrophic bacteria, yeast, mould, gram positive bacteria, or *Listeria* in food products.

WO9816124A1 relates to a food or beverage or animal feed composition which includes an antimycotic effective amount of *propionibacteria* metabolites.

OBJECT OF THE INVENTION

It is an object of embodiments of the invention to provide improved strains of *Propionibacterium* as well as preparations and compositions, such as fermentation broths, protective cultures, final food or feed product comprising such improved *Propionibacterium* alone or in combination with bacteria of the genus *Lactobacillus*.

It is an object of embodiments of the invention to provide methods for the controlling of growth of a contaminant, such as a bacteria, yeast or mould by using these novel strains of *Propionibacterium*.

SUMMARY OF THE INVENTION

It has been found by the present inventor(s) that novel strains of *Propionibacterium* have improved properties in terms of being able to control of growth of a contaminant, such as a bacteria, yeast or mould.

So, in a first aspect the present invention relates to a bacteria of the genus *Propionibacterium* selected from the list consisting of:
  a. *Propionibacterium acidipropionici* DSM 25845;
  b. *Propionibacterium freudenreichii* subsp. *shermanii* DSM 25846;
  c. *Propionibacterium freudenreichii* DSM 25847;
  d. *Propionibacterium thoenii* DSM 25848; and
  e. *Propionibacterium thoenii* DSM 25849; or functional equivalents thereof.

In a second aspect the present invention relates to a bacterial preparation, characterized in that it comprises a *Propionibacterium* selected from the list consisting of:
  a. *Propionibacterium acidipropionici* DSM 25845;
  b. *Propionibacterium freudenreichii* subsp. *shermanii* DSM 25846;
  c. *Propionibacterium freudenreichii* DSM 25847;
  d. *Propionibacterium thoenii* DSM 25848; and
  e. *Propionibacterium thoenii* DSM 25849;
or functional equivalents thereof, alone or in combination with a bacterium of the genus *Lactobacillus*, with any other strain of the bacterium *Propionibacterium*, or with both.

In a third aspect the present invention relates to the use of bacteria of the genus *Propionibacterium* selected from the list consisting of:
  a. *Propionibacterium acidipropionici* DSM 25845;
  b. *Propionibacterium freudenreichii* subsp. *shermanii* DSM 25846;
  c. *Propionibacterium freudenreichii* DSM 25847;
  d. *Propionibacterium thoenii* DSM 25848; and e. *Propionibacterium thoenii* DSM 25849;
or functional equivalents thereof, in the preparation of a final food or feed product.

In a further aspect the present invention relates to a composition, such as a protective culture or a final food or feed product, comprising viable bacteria of the genus *Propionibacterium* selected from the list consisting of:
a. *Propionibacterium acidipropionici* DSM 25845;
b. *Propionibacterium freudenreichii* subsp. *shermanii* DSM 25846;
c. *Propionibacterium freudenreichii* DSM 25847;
d. *Propionibacterium thoenii* DSM 25848; and
e. *Propionibacterium thoenii* DSM 25849;
or functional equivalents thereof.

In a further aspect the present invention relates to the use of a bacterial preparation comprising a *Propionibacterium* selected from the list consisting of:
a. *Propionibacterium acidipropionici* DSM 25845;
b. *Propionibacterium freudenreichii* subsp. *shermanii* DSM 25846;
c. *Propionibacterium freudenreichii* DSM 25847;
d. *Propionibacterium thoenii* DSM 25848; and
e. *Propionibacterium thoenii* DSM 25849;
or functional equivalents thereof, to control the growth of a contaminant, such as a bacteria, yeast or mould.

In a further aspect the present invention relates to a method of controlling the growth of a contaminant, such as a bacteria, yeast or mould, characterized by using a bacterial preparation comprising a *Propionibacterium* selected from the list consisting of:
a. *Propionibacterium acidipropionici* DSM 25845;
b. *Propionibacterium freudenreichii* subsp. *shermanii* DSM 25846;
c. *Propionibacterium freudenreichii* DSM 25847;
d. *Propionibacterium thoenii* DSM 25848; and
e. *Propionibacterium thoenii* DSM 25849;
or functional equivalents thereof, alone or in combination with a bacterium of the genus *Lactobacillus*, with any other strain of the bacterium *Propionibacterium*, or with both.

In a further aspect the present invention relates to a composition, such as a protective culture or a final food or feed product, comprising viable bacteria of the genus *Lactobacillus* in combination with a *Propionibacterium* selected from the list consisting of:
a. *Propionibacterium acidipropionici* DSM 25845;
b. *Propionibacterium freudenreichii* subsp. *shermanii* DSM 25846;
c. *Propionibacterium freudenreichii* DSM 25847;
d. *Propionibacterium thoenii* DSM 25848; and
e. *Propionibacterium thoenii* DSM 25849;
or functional equivalents thereof.

In some embodiments the method further comprises as step of purifying and/or concentrating said bacteria of the genus *Lactobacillus*.

In a further aspect the present invention relates to a method for controlling the growth of a contaminant, such as a bacteria, yeast or mould, in a composition, the method characterized by having in this composition the presence of a bacterial preparation according to the present invention.

In a further aspect the present invention relates to a method for storing a food or feed product, said food or feed product comprising viable bacteria of the genus *Lactobacillus*, the method comprising a step of controlling the growth of a contaminant, such as a bacteria, yeast or mould, in this food or feed product by addition to said food or feed product of a bacteria according to the invention or a bacterial preparation according to the invention.

LEGENDS TO THE FIGURE

FIG. 1-8 are the results of overlayer assays. The clear zones around the *propionibacteria* colonies are visible when antifungal metabolites were produced by the *propionibacteria*.

FIG. 1 *Propionibacterium freudenreichii* subsp. *shermanii* DSM 25846 and its inhibitory effect on *Penicillium* sp. DCS 436.

Figure 2:

FIG. 2 *Propionibacterium freudenreichii* DSM 25847 and its inhibitory effect on *Penicillium* sp. DCS 436.

Figure 3:
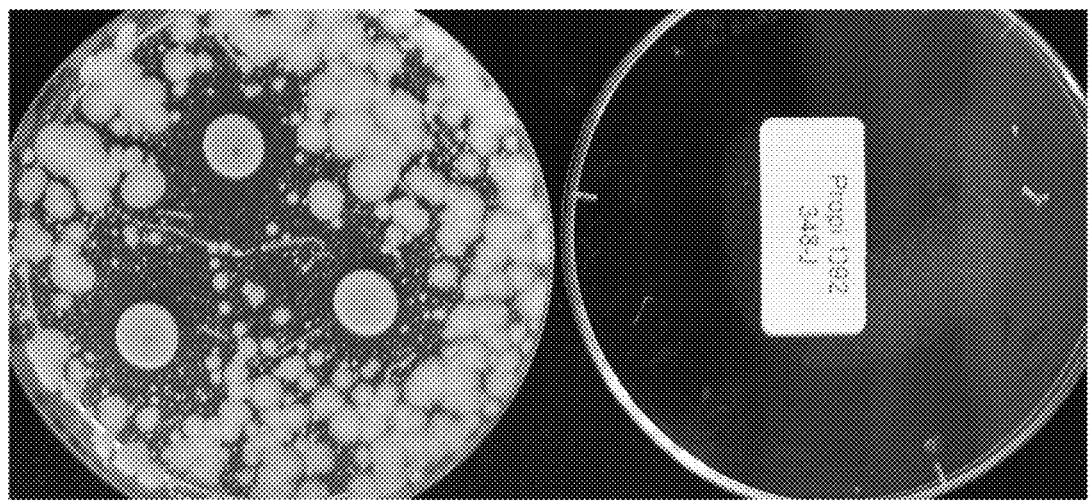

FIG. 3 *Propionibacterium freudenreichii* DSM 25847 and its inhibitory effect on *Debaryomyces hansenii* DCS 605.

Figure 4:
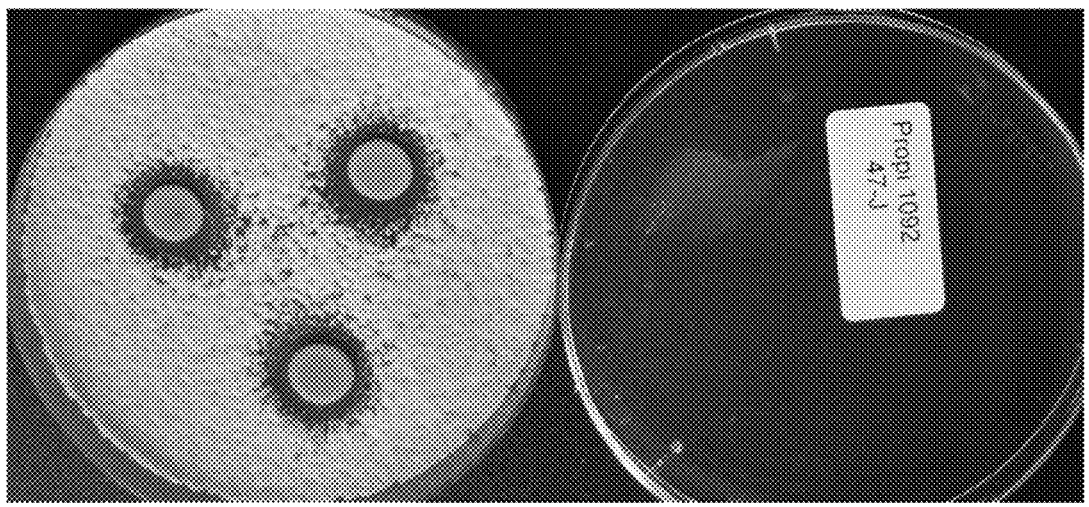

FIG. 4 *Propionibacterium freudenreichii* DSM 25847 and its inhibitory effect on *Penicillium* sp. DCS 1540.

Figure 5:

FIG. 5 *Propionibacterium acidipropionici* DSM 25845 and its inhibitory effect on *Candida sake* DCS 1055.

Figure 6:
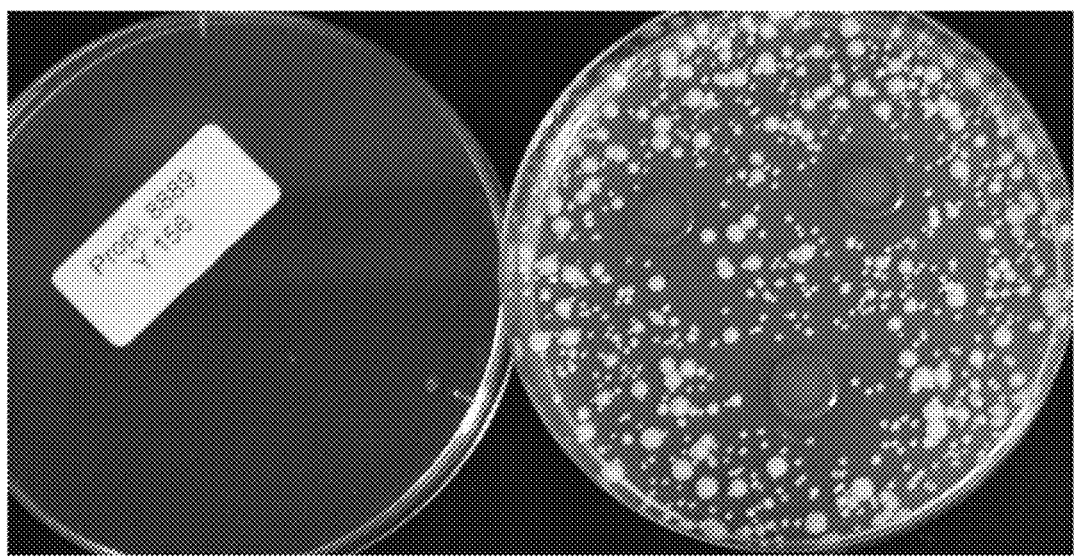

FIG. 6 *Propionibacterium thoenii* DSM 25848 and its inhibitory effect on *Candida sake* DCS 1055.

Figure 7:

FIG. 7 *Propionibacterium thoenii* DSM 25848 and its inhibitory effect on *Candida sake* DCS 1057.

Figure 8:
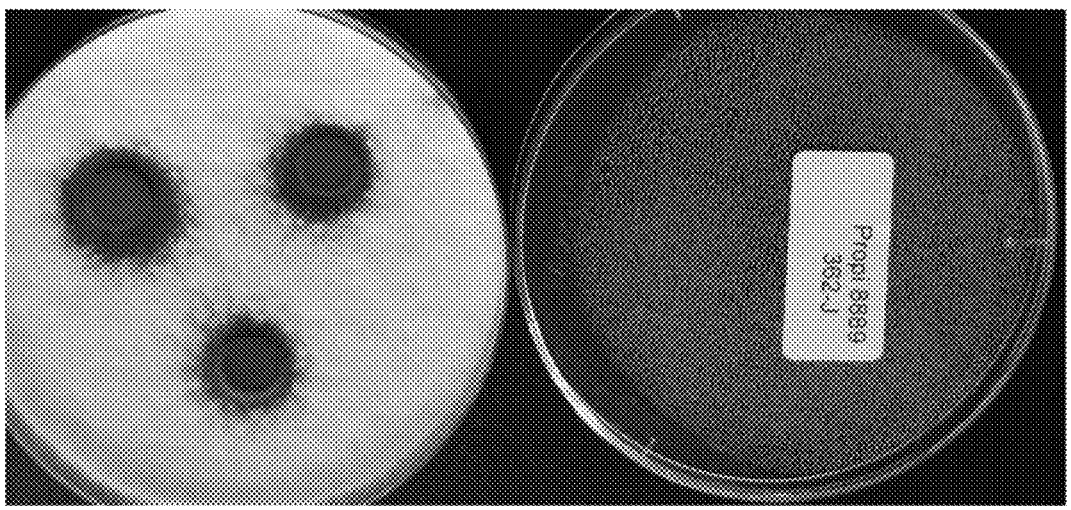

FIG. 8 *Propionibacterium thoenii* DSM 25848 and its inhibitory effect on *Fusarium* sp. DCS 1105.

Figure 9:
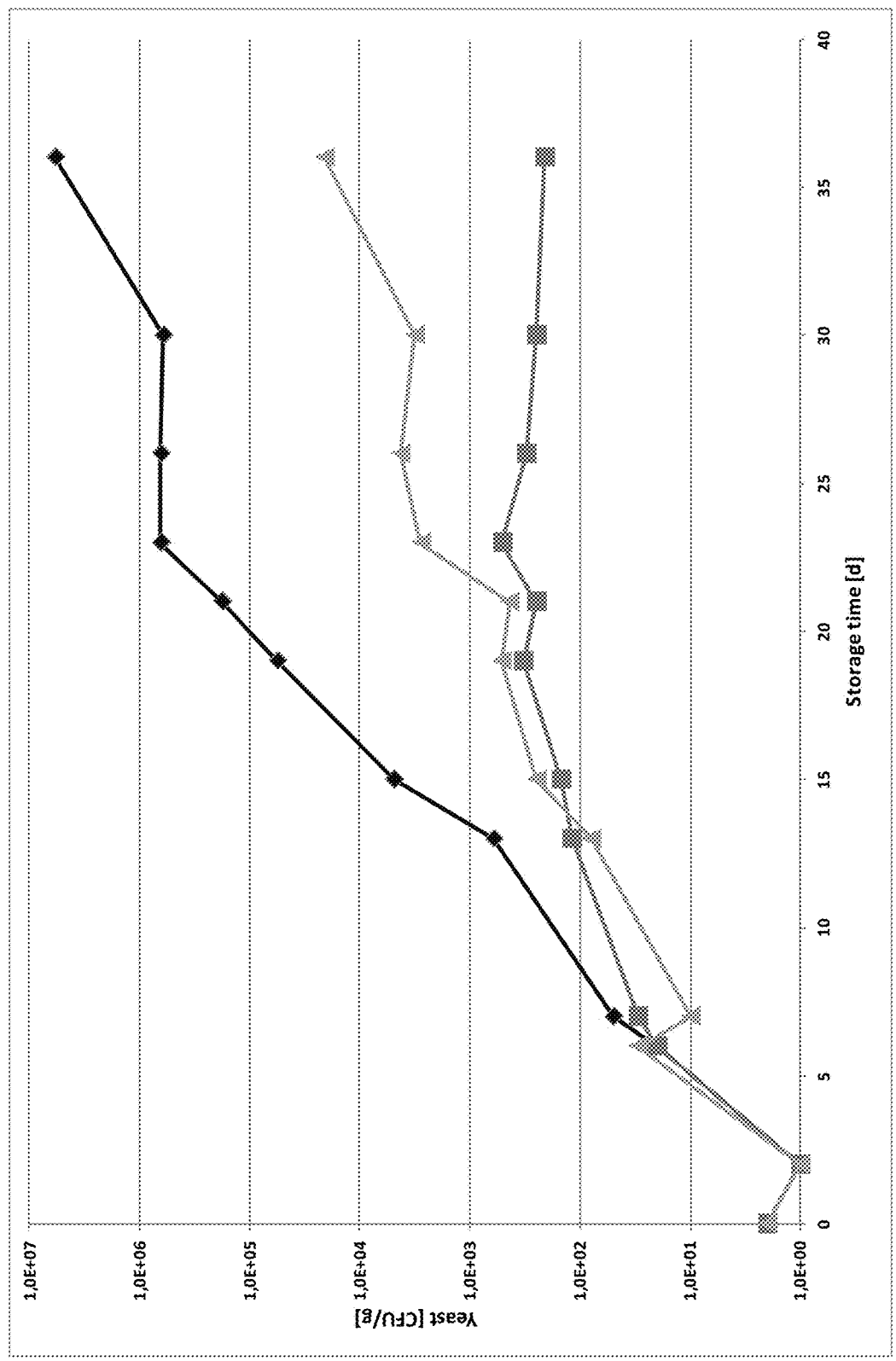

FIG. 9: Levels of yeasts (*Rhodotorula mucilaginosa* DCS 1087 and *Debaryomyces hansenii* DCS 605) in 3 different batches of yogurt with and without antifungal cultures stored at 6° C. No protective culture (♦), freeze-dried blend of *Propionibacterium freudenreichii* subsp. *shermanii* DSM 25846 and *Lactobacillus rhamnosus* DSM 7061 (■), freeze-dried blend of *Propionibacterium freudenreichii* subsp. *shermanii* DSM 25846 and *Lactobacillus paracasei* subsp. *paracasei* DSM 14514 (▲).

Figure 10:
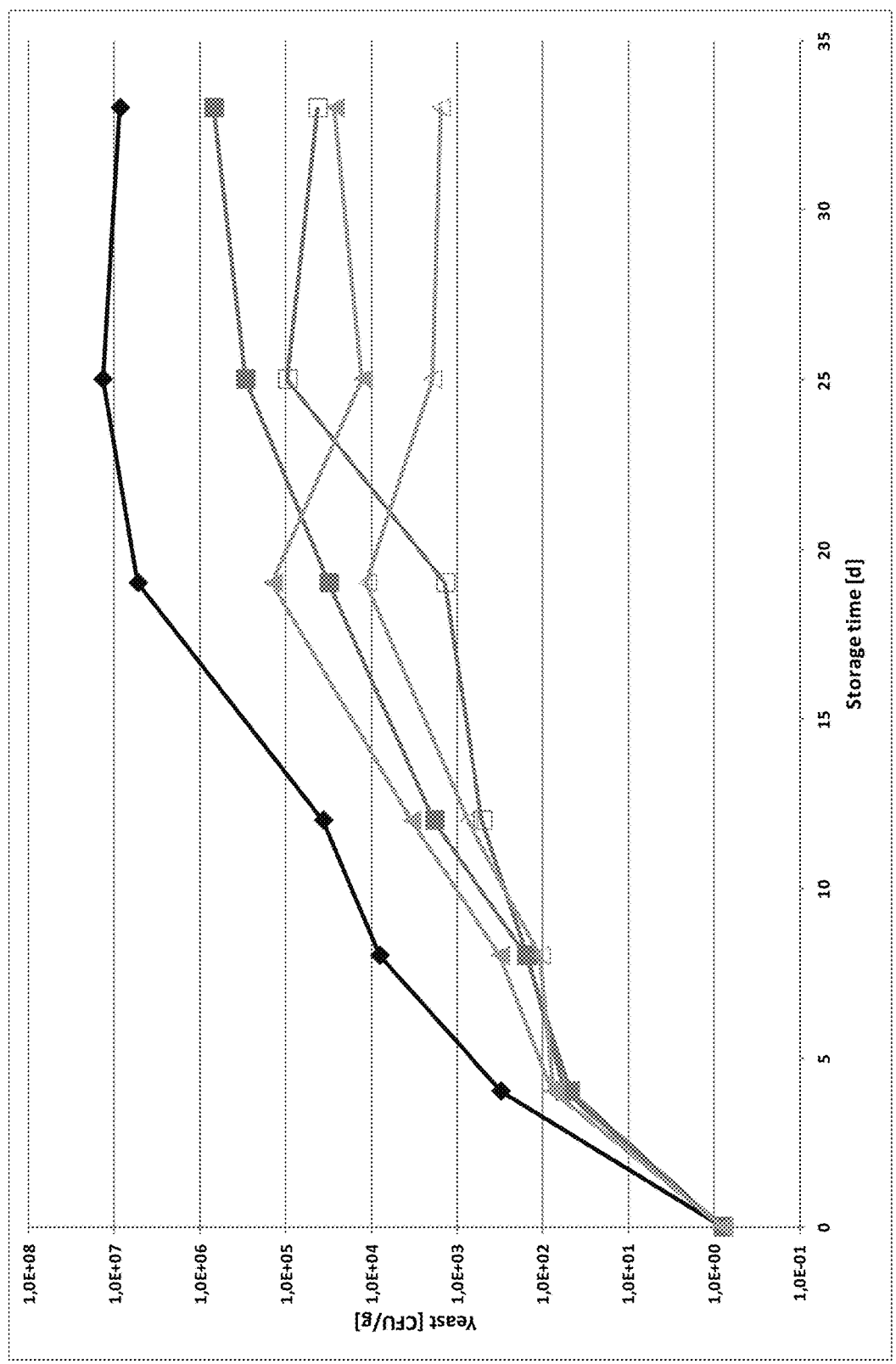

FIG. 10: Levels of yeasts (*Rhodotorula mucilaginosa* DCS 1087 and *Debaryomyces hansenii* DCS 605) in 3 different batches of yogurt with and without antifungal cultures stored at 6° C. No protective culture (♦), freeze-dried blend of *Propionibacterium freudenreichii* subsp. *shermanii* DSM 25846 and *Lactobacillus rhamnosus* DSM 7061 (■), frozen blend of *Propionibacterium freudenreichii* subsp. *shermanii* DSM 25846 and *Lactobacillus rhamnosus* DSM 7061 (□), freeze-dried blend of *Propionibacterium freudenreichii* subsp. *shermanii* DSM 25846 and *Lactobacillus paracasei* subsp. *paracasei* DSM 14514 (▲), frozen blend of *Propionibacterium freudenreichii* subsp. *shermanii* DSM 25846 and *Lactobacillus paracasei* subsp. *paracasei* DSM 14514 (Δ).

DETAILED DISCLOSURE OF THE INVENTION

The antifungal effects of the commercial available antifungal cultures HOLDBAC™ YM-B and HOLDBAC™ YM-C (DuPont, Denmark) has been demonstrated in various challenge studies in different types of fermented dairy products like yogurt, fresh cheese, sour cream and white brined cheese. Furthermore the application of HOLDBAC™ YM-B and HOLDBAC™ YM-C was evaluated in internal trials in Gouda-type cheese. The results demonstrated a delayed outgrowth of spoilage moulds on the cheeses prepared with either HOLDBAC™ YM-B or HOLDBAC™ YM-C compared to a reference without protective culture added. It is envisioned, that the mere presence of the *Propionibacterium* strain potentially may induce the formation of antifungal metabolites by the *Lactobacillus* strain. The inventors of the present invention have demonstrated that the major part of the antifungal activity is coming from the *Lactobacillus* and combinations of live *lactobacilli* with *propionibacteria* that express antifungal activity as well.

The present invention concerns improved *propionibacteria* having inhibition activity against yeast and moulds. The bacteria are suitable for the preservation of goods (e.g. food or feed).

As described in the examples, the strains were screened in an agar assay.

The strains may be used to develop antifungal cultures especially for dairy applications. Using antifungal *lactobacilli*, antifungal cultures based on the co-culture concept of HOLDBAC™ YM would be possible, for use in, e.g., yoghurt (including drinking yoghurt), sour cream, semi-hard and hard cheese, cottage cheese, fresh cheese, cream cheese, and white-brined cheese.

Other food applications like e.g. sourdough may be a potential application as well as protection of feed products, such as e.g. silage.

Definitions

As used herein the term "viable" refers to bacterial cells with the potential to have an active metabolism, to survive, grow, or multiply.

As used herein the term "protective culture of *Lactobacillus*" refers to composition comprising live *Lactobacillus* (pure cultures or culture concentrates), which is not a final food product suitable for consumption, but which is added to food products with the aim of reducing risks by pathogenic or toxinogenic microorganisms. Included within this definition are compositions, such as fermentation media and concentrated preparations thereof, wherein *Lactobacillus* is grown in a suitable medium.

As used herein the term "protective culture of *Propionibacterium*" refers to composition comprising live *Propionibacteria* (pure cultures or culture concentrates), which is not a final food product suitable for consumption, but which is added to food products with the aim of reducing risks by pathogenic or toxinogenic microorganisms. Included within this definition are compositions, such as fermentation media and concentrated preparations thereof, wherein *Propionibacterium* is grown in a suitable medium.

The European Food and Feed Cultures Association (EFFCA) has characterized protective cultures as follows: The term "Protective Cultures" has been applied to microbial food cultures (MFC) exhibiting a metabolic activity contributing to inhibit or control the growth of undesired microorganisms in food. These undesired microorganisms could be pathogenic or toxinogenic bacteria and fungi but spoilage causing species may also be included.

Protective cultures are considered as an integral part of starter cultures, which are the traditional tools of food technology used to produce fermented food such as cheese, yoghurt, certain sausages, wine etc. It is a general property of fermented foods that these possess a longer shelf life than the non-fermented raw materials (for instance cheese, has a much longer shelf-life than milk). This property is the result of the active metabolism of the fermenting culture, conducting its actions through a complex system of competition for nutrients and binding sites and by production of inhibitory metabolites like organic acids, hydrogen peroxide, diacetyl, reuterin and bacteriocins.

Depending on the specific cultures used the cultures commonly form numerous properties that are of sensory and nutritive value to the food product, too. In this way the same starter culture species used in fermentation processes have also been applied to food in order to make use of the "bioprotective" potential with or without sensory impact. For these starter cultures the term protective culture, has been applied.

Their usage is not limited to "classic" fermented foods but also plays an important role when their metabolic activities take place in food with a neutral pH and high water activity, which are subject to increased risk of growth of food pathogens. The application of "protective cultures" constitutes an additional measure to improve food hygiene and should not permit a neglecting of any measure of good manufacturing practice ensuring the high standard of food safety.

Protective cultures are an integral part of starter cultures rather than additives. It is clear that these cultures develop their protective and beneficial potential, like all starter cultures, as a result of their metabolic activity in or on the food. (EFFCA, December 2011).

The protective culture is added together with a starter culture to the food or feed matrix before the fermentation of the food or feed. Thus the protective culture undergoes the fermentation step and is able to grow and/or to be metabolic active. The starter culture is needed to produce fermented foods like yogurt, cheese and sour cream and contributes to the desired product changes in taste, texture and flavour development. In addition to this, protective cultures are added to the food to limit the growth of pathogenic or spoilage bacteria and thus reduce the risk of food poisonings and protect the shelf-life.

As used herein the term "final food or feed product" refers to a composition suitable for consumption, such as for human or animal consumption in the form of a food or feeding stuff.

The term "contaminant" as used herein refers to any unwanted and unintentional growth of any microorganism, such as bacteria, fungi, such as yeast or a mould. In some instances the contaminant may cause disease. However, often the contaminant just degrade and deteriorate the product wherein it is found and/or give an unpleasant and unwanted taste or mouth feel.

In some embodiments the contaminant is a fungi selected from the list consisting of *Penicillium* spp., *Penicillium brevicompactum, Penicillium solitum, Penicillium glabrum, Penicillium corylophilum, Penicillium roqueforti, Aspergillus* sp., *Aspergillus ochraceus, Aspergillus parasiticus, Aspergillus versicolor, Aspergillus niger, Eurotium* spp., *Fusarium* spp., *Candida* spp., *Candida colliculosa, Candida famata, Candida guilliermondii, Candida kefyr, Candida lambica, Candida lipolytica, Candida lusitaniae, Candida sake, Candida sphaerica, Candida parapsilosis, Candida pelliculosa, Candida rugosa, Candida zeylanoides, Debaryomyces* spp., *Debaryomyces hansenii, Kluyveromyces* spp., *Kluyveromyces marxianus, Rhodotorula* spp., *Rhodotorula mucilaginosa, Saccharomyces* spp., *Saccharomyces cerevisiae, Saccharomyces servazzii*, and *Geotrichum* spp., *Geotrichum candidum*.

In some embodiments the contaminant is a bacteria different from the specific *Lactobacillus* strain used in the methods according to the invention, selected from the list consisting of *Listeria monocytogenes, Pseudomonas* sp., *Staphylococcus aureus, Bacillus* sp., *Lactobacillus* sp., *Leuconostoc* sp., *Clostridium* sp., *Enterobacteriaceae* like *Citrobacter* sp., *Enterobacter* sp., *Escherichia* sp., *Klebsiella* sp., *Salmonella* sp.

Lactobacillus

As used herein the term "bacteria of the genus *Lactobacillus*" refers to any strain of the genus *Lactobacillus*, such as strains of *Lactobacillus* that may be used for the production of yogurt, cheese, sauerkraut, pickles, beer, wine, cider, kimchi, cocoa, and other fermented foods, as well as animal feeds, such as silage. The term *Lactobacillus* is intended to encompass organisms described in (http://www.bacterio.cict.fr/l/Lactobacillus.html), and in particular including *L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* subsp. *delbrueckii, L. delbrueckii* subsp. *bulgaricus, L. delbrueckii* subsp. *lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. graminis, L. hammesii, L. hamsteri, L. harbinensis, L. hayakitensis, L. helveticus, L. hilgardii, L. homohiochii, L. iners, L. ingluviei, L. intestinalis, L. jensenii, L. johnsonii, L. kalixensis, L. kefiranofaciens, L. kefiri, L. kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracollinoides, L. parafarraginis, L. parakefiri, L. paralimentarius, L. paraplantarum, L. pentosus, L. perolens, L. plantarum, L. pontis, L. psittaci, L. rennini, L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmo/densis, L. vini, L. vitulinus, L. zeae*, and *L. zymae*, as well as variants thereof.

The term *Lactobacillus* is intended to encompass any specific *Lactobacillus* strain described in EP0576780, EP1308506 EP1796698, EP2245943, EP1530642, EP1740726, WO 03/040349 WO/2006/032542, WO/2007/132359, WO/2004/013343, and WO/2010/081138.

In some embodiments the *Lactobacillus* strain is selected from *Lactobacillus paracasei* subsp. *paracasei* DSM 14514, and *Lactobacillus plantarum* DSM 25833.

Propionibacterium

As used herein the term "any other strain of the bacterium *Propionibacterium*" refers to any strain of the genus *Propionibacterium* including the species *Propionibacterium acidifaciens, Propionibacterium acidipropionici, Propionibacterium acnes, Propionibacterium australiense, Propionibacterium avidum, Propionibacterium cyclohexanicum, Propionibacterium freudenreichii* subsp. *freudenreichii, Propionibacterium freudenreichii* subsp. *shermanii, Propionibacterium granulosum, Propionibacterium jensenii, Propionibacterium microaerophilum, Propionibacterium propionicum*, and *Propionibacterium thoenii*, as well as variants thereof. The term is intended to encompass specific strains described in the present disclosure and in any of EP0576780, EP1308506, WO03/040349, and US4728516, including *Propionibacterium freudenreichii* subsp. *shermanii* DSM 7067.

Specific Embodiments of the Invention

In some embodiments the bacterial preparation according to the present invention is a cell suspension in fermentation broth, alone or in combination with a bacterium of the genus *Lactobacillus* or another strain of the *Propionibacterium*.

In some embodiments the bacterial preparation according to the present invention further comprises a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

In some embodiments, the bacterial preparation comprises a strain of *Propionibacterium* selected from *Propionibacterium acidipropionici* DSM 25845; *Propionibacterium freudenreichii* subsp. *shermanii* DSM 25846; *Propionibacterium freudenreichii* DSM 25847; *Propionibacterium thoenii* DSM 25848; *Propionibacterium thoenii* DSM 25849, and *Propionibacterium freudenreichii* subsp. *shermanii* DSM 7067, or a combination of any thereof.

In some embodiments, the bacterial preparation according to the present invention comprises *Propionibacterium acidipropionici* DSM 25845 and a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

In some embodiments, the bacterial preparation according to the present invention comprises *Propionibacterium freudenreichii* subsp. *shermanii* DSM 25846 and a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

In some embodiments, the bacterial preparation according to the present invention comprises *Propionibacterium freudenreichii* DSM 25847 and a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

In some embodiments, the bacterial preparation according to the present invention comprises *Propionibacterium thoenii* DSM 25848 and a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

In some embodiments, the bacterial preparation according to the present invention comprises *Propionibacterium thoenii* DSM 25849 and a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

In some embodiments, the bacterial preparation according to the present invention comprises *Propionibacterium freudenreichii* subsp. *shermanii* DSM 7067 and a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus*

*plantarum* DSM 25835; *Lactobacillus plantarum* DSM 25836; *Lactobacillus plantarum* DSM 25837; and *Lactobacillus rhamnosus* DSM 7061.

In some embodiments the bacterial preparation according to the present invention is concentrated.

In some embodiments the bacterial preparation according to the present invention is freeze-dried or frozen.

In some embodiments the bacterial preparation according to the present invention is characterized in that it additionally comprises conventional agents used for yeast and mould control, such as propionate or phenylalanine.

In some embodiments the composition according to the present invention is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a protective culture of *Propionibacterium* and said viable bacteria of the genus *Propionibacterium* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final food or feed product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final food or feed product and said viable bacteria of the genus *Propionibacterium* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition or preparation according to the present invention is a protective culture of *Lactobacillus*.

In some embodiments the composition or preparation according to the present invention is a protective culture of *Propionibacterium*.

In some embodiments the composition or preparation according to the present invention is a final food or feed product.

In some embodiments the composition according to the present invention is with or without cell remnants of said bacteria of the genus *Propionibacterium*.

In some embodiments the composition according to the present invention is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a protective culture of *Propionibacterium* and said viable bacteria of the genus *Propionibacterium* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a protective culture of *Propionibacterium* and said viable bacteria of the genus *Propionibacterium* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition according to the present invention is a final product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

In some embodiments the composition or preparation according to the present invention is used for the preparation of a food product of feed product, such as a milk product. In some embodiments the food product is selected from the group consisting of dairy products, yoghurt, drinking yogurt, cheese, such as fresh cheese, cream cheese, cottage cheese, semi-soft and soft cheese, semi-hard and hard cheese, white brine cheese, sour milk products, and sour cream, sauerkraut, pickles, beer, wine, cider, kimchi, cocoa, sour dough and other fermented foods, as well as animal feeds, such as silage.

In some embodiments according to the present invention, the bacteria of the genus *Lactobacillus* is selected from the list consisting of

*Lactobacillus paracasei* subsp. *paracasei* DSM 14514;
*Lactobacillus paracasei* subsp. *paracasei* DSM 25832;
*Lactobacillus plantarum* DSM 25833;
*Lactobacillus plantarum* DSM 25834;
*Lactobacillus plantarum* DSM 25835;
*Lactobacillus plantarum* DSM 25836;
*Lactobacillus plantarum* DSM 25837; and
*Lactobacillus rhamnosus* DSM 7061.

Numbered embodiments according to the invention:

1. Bacteria of the genus *Propionibacterium* selected from the list consisting of:
    a. *Propionibacterium acidipropionici* DSM 25845;
    b. *Propionibacterium freudenreichii* subsp. *shermanii* DSM 25846;
    c. *Propionibacterium freudenreichii* DSM 25847;
    d. *Propionibacterium thoenii* DSM 25848; and
    e. *Propionibacterium thoenii* DSM 25849; or functional equivalents thereof.

2. A bacterial preparation, characterized in that it comprises a *Propionibacterium* selected from the list consisting of:
    a. *Propionibacterium acidipropionici* DSM 25845;
    b. *Propionibacterium freudenreichii* subsp. *shermanii* DSM 25846;
    c. *Propionibacterium freudenreichii* DSM 25847;
    d. *Propionibacterium thoenii* DSM 25848; and
    e. *Propionibacterium thoenii* DSM 25849;
or functional equivalents thereof, alone or in combination with a bacterium of the genus *Lactobacillus*, with any other strain of the genus *Propionibacterium*, or with both.

3. A bacterial preparation according to embodiment 2, which is a cell suspension in fermentation broth, alone or in combination with a bacterium of the genus *Lactobacillus*, with another strain of the *Propionibacterium*, or with both.

4. A bacterial preparation according to any one of embodiments 2-3, characterized in that it comprises a strain of *Lactobacillus* selected from *Lactobacillus paracasei* subsp. *paracasei* DSM 14514; *Lactobacillus paracasei* subsp. *paracasei* DSM 25832; *Lactobacillus plantarum* DSM 25833; *Lactobacillus plantarum* DSM 25834; *Lactobacillus plantarum* DSM 25835; *Lactobacillus plantarum* DSM 25836; *Lactobacillus plantarum* DSM 25837; and *Lactobacillus rhamnosus* DSM 7061.

5. A bacterial preparation according to any one of embodiments 2-4, which preparation is concentrated.

6. A bacterial preparation according to any one of embodiments 2-4, which preparation is freeze-dried.

7. A bacterial preparation according to any one of embodiments 2-6, characterized in that it additionally comprises conventional agents used for yeast and mould control, such as propionate or phenylalanine.

8. Use of bacteria of the genus *Propionibacterium* selected from the list consisting of:
    a. *Propionibacterium acidipropionici* DSM 25845;
    b. *Propionibacterium freudenreichii* subsp. *shermanii* DSM 25846;
    c. *Propionibacterium freudenreichii* DSM 25847;
    d. *Propionibacterium thoenii* DSM 25848; and
    e. *Propionibacterium thoenii* DSM 25849;
or functional equivalents thereof, in the preparation of a final food or feed product.

9. Use of a bacterial preparation comprising the a *Propionibacterium* selected from the list consisting of:
    a. *Propionibacterium acidipropionici* DSM 25845;
    b. *Propionibacterium freudenreichii* subsp. *shermanii* DSM 25846;
    c. *Propionibacterium freudenreichii* DSM 25847;
    d. *Propionibacterium thoenii* DSM 25848; and
    e. *Propionibacterium thoenii* DSM 25849;
or functional equivalents thereof, to control the growth of a contaminant, such as a bacteria, yeast or mould.

10. A method of controlling the growth of a contaminant, such as a bacteria, yeast or mould, characterized by using a bacterial preparation comprising a *Propionibacterium* selected from the list consisting of:
    a. *Propionibacterium acidipropionici* DSM 25845;
    b. *Propionibacterium freudenreichii* subsp. *shermanii* DSM 25846;
    c. *Propionibacterium freudenreichii* DSM 25847;
    d. *Propionibacterium thoenii* DSM 25848; and
    e. *Propionibacterium thoenii* DSM 25849;
or functional equivalents thereof, alone or in combination with a bacterium of the genus *Lactobacillus*, with another strain of the genus *Propionibacterium*, or with both.

11. A composition, such as a protective culture or a final food or feed product, comprising viable bacteria of the genus *Lactobacillus* in combination with a *Propionibacterium* selected from the list consisting of:
    a. *Propionibacterium acidipropionici* DSM 25845;
    b. *Propionibacterium freudenreichii* subsp. *shermanii* DSM 25846;
    c. *Propionibacterium freudenreichii* DSM 25847;
    d. *Propionibacterium thoenii* DSM 25848; and
    e. *Propionibacterium thoenii* DSM 25849;
or functional equivalents thereof.

12. The composition according to embodiment 11, wherein said composition is a protective culture of *Lactobacillus* and said viable bacteria of the genus *Lactobacillus* is present in an amount of at least $10^7$ CFU/g or ml, such as at least $5\times10^7$ CFU/g or ml, such as at least $10^8$ CFU/g or ml, such as at least $10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

13. The composition according to embodiment 11, wherein said composition is a final food or feed product and said viable bacteria of the genus *Lactobacillus* is present in an amount of at least $10^5$ CFU/g or ml, such as at least $5\times10^5$ CFU/g or ml, such as at least $10^6$ CFU/g or ml, such as at least $5\times10^6$ CFU/g or ml, such as at least $10^7$ CFU/g or ml, such as at least $5\times10^7$ CFU/g or ml, such as at least $10^8$ CFU/g or ml, such as at least $5\times10^8$ CFU/g or ml, such as at least $10^9$ CFU/g or ml, such as at least $5\times10^9$ CFU/g or ml, such as at least $10^{10}$ CFU/g or ml, such as at least $5\times10^{10}$ CFU/g or ml, such as at least $10^{11}$ CFU/g or ml, such as at least $5\times10^{11}$ CFU/g or ml, such as at least $10^{12}$ CFU/g or ml, such as at least $5\times10^{12}$ CFU/g or ml, such as at least $10^{13}$ CFU/g or ml, such as at least $5\times10^{13}$ CFU/g or ml of composition.

14. The composition according to any one of embodiments 11-13 or preparation according to embodiments 2-7, which is or is used for the preparation of a food product of feed product, such as a milk product.

15. The composition according to embodiment 14, wherein said food product is selected from the group consisting of dairy products, yoghurt, drinking yogurt, cheese, such as fresh cheese, cream cheese, cottage cheese, semi-soft and soft cheese, semi-hard and hard cheese, white brine cheese, sour milk products, and sour cream, sauerkraut, pickles, beer, wine, cider, kimchi, cocoa, sour dough and other fermented foods, as well as animal feeds, such as silage.

16. The composition according to any one of embodiments 11-13 or preparation according to embodiments 2-7, wherein said bacteria of the genus *Lactobacillus* is selected from the list consisting of

*Lactobacillus paracasei* subsp. *paracasei* DSM 14514;
*Lactobacillus paracasei* subsp. *paracasei* DSM 25832;
*Lactobacillus plantarum* DSM 25833;
*Lactobacillus plantarum* DSM 25834;
*Lactobacillus plantarum* DSM 25835;
*Lactobacillus plantarum* DSM 25836;
*Lactobacillus plantarum* DSM 25837; and
*Lactobacillus rhamnosus* DSM 7061, or a combination of any thereof.

17. Use of the composition according to any one of embodiments 11-16 to control the growth of a contaminant, such as a bacteria, yeast or mould.

EXAMPLE 1

*Propionibacteria* Test Strains
The following *propionibacteria* strains were used:
*Propionibacterium acidipropionici* DSM 25845;
*Propionibacterium freudenreichii* subsp. *shermanii* DSM 25846;
*Propionibacterium freudenreichii* DSM 25847;
*Propionibacterium thoenii* DSM 25848; and
*Propionibacterium thoenii* DSM 25849;

Cultivation of *Propionibacteria*

The *propionibacteria* were propagated in sodium lactate broth that consisted of 2% peptone from casein (Merck KGaA, Darmstadt, Germany), 1% yeast extract (Merck) and 1.6% sodium lactate solution 50% (Merck) at 30° C. in anaerobic jars. A passage was done by adding 0.1 ml from the pre-cultures to 10 ml sodium lactate broth, cultivation as described above. The cultures were kept at 4-6° C. prior to use.

Yeast and Mould Indicator Strains
In the following the yeast and mould strains are listed in table 1 and 2.

TABLE 1

List of yeast strains used in the screening for antifungal activity

| Strain Number | Strain name | Origin |
|---|---|---|
| DCS 298 | *Candida parapsilosis* | Miescher[1] |
| DCS 605 | *Debaryomyces hansenii* | DSM 70238[2] |
| DCS 1037 | *Debaryomyces hansenii* | DuPont A/S[3] |
| DSC 1048 | *Candida lusitaniae* | DuPont A/S |
| DSC 1055 | *Candida sake* | DuPont A/S |
| DSC 1057 | *Candida sake* | DuPont A/S |

[1]Miescher, S. 1999. Antimicrobial and autolytic systems of dairy propionibacteria. PhD thesis No. 13486. ETH Zürich, Switzerland.
[2]Deutsche Sammlung von Mikroorganismen and Zellkulturen GmbH, Braunschweig, Germany
[3]Danisco Nutrition Biosciences ApS, Brabrand, Denmark Prior to use, the yeasts were cultivated in a broth consisted of 2% glucose (vwr, Herlev, Denmark), 0.5% yeast extract (Oxoid Limited, Basingstoke, United Kingdom) and 0.01% peptone from casein (Oxoid) dissolved in a potassium di-hydrogen phosphate solution (312 µmol/l, pH 7.20±0.10). Sterile glycerol was added in a concentration of 33% v/v to the medium with grown yeast before storage in cryo tubes at −80° C. After freezing the yeast cultures were enumerated on malt extract agar (Oxoid).

TABLE 2

List of mould strains used in the screening for antifungal activity

| Strain Number | Strain name | Origin |
|---|---|---|
| DCS 434 | *Penicillium* sp. | DuPont A/S |
| DCS 435 | *Penicillium* sp. | DuPont A/S |
| DCS 436 | *Penicillium* sp. | DuPont A/S |
| DCS 437 | *Penicillium* sp. | DuPont A/S |
| DCS 708 | *Aspergillus ochraceus* | CBS 116.39[4] |
| DCS 709 | *Aspergillus parasiticus* | CBS 100926 |
| DCS 1065 | *Penicillium* sp. | DuPont A/S |
| DCS 1069 | *Aspergillus versicolor* | DSM 63292 |
| DCS 1093 | *Penicillium roqueforti* | DTU 531[5] |
| DCS 1099 | *Eurotium* sp. | DTU 123 |
| DCS 1105 | *Fusarium* sp. | DTU 40496 |
| DCS 1106 | *Fusarium* sp. | DTU 40872 |
| DCS 1113 | *Penicillium corylophilum* | DSM 62831 |
| DCS 1115 | *Aspergillus niger* | DSM 737 |
| DCS 1558 | *Penicillium* sp. | DuPont A/S |
| DCS 1540 | *Penicillium* sp. | DuPont A/S |
| DCS 1541 | *Penicillium* sp. | DuPont A/S |

[3]Danisco Nutrition Biosciences ApS, Brabrand, Denmark
[4]Centraalbureau voor Schimmelcultures, Utrecht, The Netherlands
[5]Danmarks Tekniske Universitet, Lyngby, Denmark The mould strains were cultivated on malt extract agar slants (Oxoid) until sporulation was visible. The spores were harvested by adding twice 5 ml sterile tap water supplemented with 0.01% Tween 80 (Merck). Sterile glycerol was added in a concentration of 33% v/v to the spore solutions before storage in cryo tubes at −80° C. A spore count was made after freezing on malt extract agar (Oxoid).

Overlayer Assay

The *propionibacteria* test strains were spot inoculated (three spots per plate) on sodium lactate agar that consisted of 2% tryptone (Oxoid), 1% yeast extract (Oxoid), 1.6% sodium lactate solution 50% (Merck) and 1.5% agar agar (Merck). The plates were incubated at 30° C. in anaerobic jars.

The plates with grown colonies of the *propionibacteria* were overlaid with malt extract soft agar consisted of 2% malt extract broth (Oxoid) and 0.8% agar agar (Merck) tempered to 47° C. containing either $10^4$ yeast cells/ml or $10^4$ mould spores/ml. The overlaid plates were incubated for 3-5 days at 25° C. and inspected for inhibition zones around the test colonies.

As a growth control agar plates without spotted test strains were prepared for each indicator organisms. The area of the zones was graded as follows:

| | |
|---|---|
| No inhibition, plate fully overgrown | − |
| No fungal growth on the spot | (+) |
| No fungal growth for 5 mm around the spot | + |

Results

Five *propionibacteria* were tested for antifungal activities. Therefore, the strains were spot inoculated on sodium lactate agar plates on which the fungi listed in table 1 and 2 were applied incorporated in malt extract soft agar. The plates were stored at 25° C. and inspected for inhibition zones around the *lactobacilli* colonies.

All five tested *propionibacteria* showed antifungal activity in the applied overlayer assay as summarised in table 3.

The *propionibacteria* showed only slightly different inhibition spectra. The majority of the moulds were more sensitive and inhibited to a higher extent than the tested yeast strains.

TABLE 3

Antifungal activities of selected *Propionibacterium* strains in an overlayer assay

| | P. acidipropionici DSM 25845 | P. freudenreichii subsp. shermanii DSM 25846 | P. freudenreichii DSM 25847 | P. thoenii DSM 25848 | P. thoenii DSM 25849 |
|---|---|---|---|---|---|
| *Candida parapsilosis* DCS 298 | (+) | (+) | (+) | (+) | − |
| *Debaryomyces hansenii* DCS 605 | (+) | (+) | (+) | (+) | (+) |
| *Debaryomyces hansenii* DCS 1037 | (+) | (+) | (+) | (+) | (+) |
| *Candida lusitaniae* DCS 1048 | − | (+) | − | (+) | (+) |
| *Candida sake* DCS 1055 | (+) | (+) | (+) | + | (+) |
| *Candida sake* DCS 1057 | − | − | − | (+) | (+) |
| *Penicillium* sp. DCS 434 | (+) | + | + | (+) | + |
| *Penicillium* sp. DCS 435 | + | + | + | + | + |
| *Penicillium* sp. DCS 436 | + | + | + | + | + |
| *Penicillium* sp. DCS 437 | + | + | (+) | + | + |
| *Aspergillus ochraceus* DCS 708 | (+) | (+) | (+) | (+) | (+) |
| *Aspergillus parasiticus* DCS 709 | (+) | (+) | (+) | (+) | (+) |
| *Penicillium* sp. DCS 1065 | + | + | + | + | + |
| *Aspergillus versicolor* DCS 1069 | + | + | + | + | + |
| *Penicillium roqueforti* DCS 1093 | − | − | (+) | − | − |
| *Eurotium* sp. DCS 1099 | (+) | (+) | (+) | (+) | (+) |
| *Fusarium* sp. DCS 1105 | (+) | + | + | + | + |
| *Fusarium* sp. DCS 1106 | (+) | + | + | + | + |
| *Penicillium corylophilum* DCS 1113 | (+) | (+) | (+) | (+) | (+) |
| *Aspergillus niger* DCS 1115 | (+) | (+) | (+) | (+) | (+) |
| *Penicillium* sp. DCS 1540 | + | + | + | + | + |
| *Penicillium* sp. DCS 1541 | + | + | + | + | + |
| *Penicillium* sp. DCS 1558 | + | (+) | + | + | + |

EXAMPLE 2

Antifungal Activity in Yogurt

The antifungal activity of *Propionibacterium freudenreichii* subsp. *shermanii* DSM 25846 was evaluated in experimental blends with either *Lactobacillus paracasei* subsp. *paracasei* DSM 14514 or *Lactobacillus rhamnosus* DSM 7061. A reference sample without protective cultures added was included for comparison. Two individual trials were carried out. In the first trial the experimental protective culture blends were prepared from freeze-dried strains. In the second trial the experimental protective culture blends were prepared from both freeze-dried and frozen strains.

Trial 1

The yogurt samples were prepared using whole milk with 3.5% fat. The milk was heat-treated for 360 seconds at 95° C. and afterwards cooled down to the fermentation temperature of 43° C. The milk was inoculated with a commercial available thermophilic yogurt starter culture. The yogurt starter culture was consisting of strains of *Streptococcus thermophilus* and *Lactobacillus delbrückii* subsp. *bulgaricus* (DuPont, Denmark). Test samples were additional inoculated with the experimental protective culture blends to give a level of either $5.0 \cdot 10^6$ CFU/ml for the blend of *Propionibacterium freudenreichii* subsp. *shermanii* DSM 25846 and *Lactobacillus rhamnosus* DSM 7061 or $5.35 \cdot 10^6$ CFU/ml for the blend of *Propionibacterium freudenreichii* subsp. *shermanii* DSM 25846 and *Lactobacillus paracasei* subsp. *paracasei* DSM 14514. The fermentation was done for about 6-7 hours at 43° C. until the pH reached 4.60. The yogurt was dispatched in sterile beakers and inoculated with a pool of yeasts. The yeast pool contained the strains *Rhodotorula mucilaginosa* DCS 1087 (CFSQE 63 (Magnusson, 3. et al 2003. FEMS Microbiology Letters 219:

129-135) and *Debaryomyces hansenii* DCS 605 (DSM 70238, Deutsche Sammlung von Mikroorganismen and Zellkulturen GmbH, Braunschweig, Germany)) and was added at a final level of 2.0E00 CFU/g of yogurt. The yogurt samples were stored for 36 days at 5° C. and yeasts were enumerated on YGC agar.

Trial 2

The yogurt samples were prepared using whole milk with 3.5% fat. The milk was heat-treated for 360 seconds at 95° C. and afterwards cooled down to the fermentation temperature of 43° C. The milk was inoculated with a commercial available thermophilic yogurt starter culture. The yogurt starter culture was consisting of strains of *Streptococcus thermophilus* and *Lactobacillus delbrückii* subsp. *bulgaricus* (DuPont, Denmark). Test samples were additional inoculated with the experimental protective culture blends to give the following cell levels: $5.0 \cdot 10^6$ CFU/ml for the freeze-dried blend of *Propionibacterium freudenreichii* subsp. *shermanii* DSM 25846 and *Lactobacillus rhamnosus* DSM 7061, $1.0 \cdot 10^7$ CFU/ml for the frozen blend of *Propionibacterium freudenreichii* subsp. *shermanii* DSM 25846 and *Lactobacillus rhamnosus* DSM 7061, and $5.35 \cdot 10^6$ CFU/ml both for the freeze-dried and frozen blend of *Propionibacterium freudenreichii* subsp. *shermanii* DSM 25846 and *Lactobacillus paracasei* subsp. *paracasei* DSM 14514. The fermentation was done for about 6-7 hours at 43° C. until the pH reached 4.60. The yogurt was dispatched in sterile beakers and inoculated with a pool of yeasts. The yeast pool contained the strains *Rhodotorula mucilaginosa* DCS 1087 and *Debaryomyces hansenii* DCS 605 and was added at a final level of 8.0E00 CFU per 10 g of yogurt. The yogurt samples were stored for 33 days at 5° C. and yeasts were enumerated on YGC agar.

Results

Trial 1

The freeze-dried experimental culture blends of *Propionibacterium freudenreichii* subsp. *shermanii* DSM 25846 with either *Lactobacillus paracasei* subsp. *paracasei* DSM 14514 or *Lactobacillus rhamnosus* DSM 7061 were evaluated for inhibitory activity against yeasts in yogurt. A reference sample without antifungal cultures was included for comparison. Portions of whole milk with 3.5% fat were fermented with a commercial yogurt culture. Test samples were inoculated additionally with the protective strains. After fermentation the yogurt samples were dispatched in beakers and inoculated with either a pool of yeasts. The samples were stored at 6° C. and the outgrowth of the added yeast strains was monitored. FIG. 1 displays the development of the yeast pool in yogurt samples with and without antifungal cultures. An increase in yeast cell counts was observed in all samples but the reference sample without antifungal cultures showed higher yeast counts than the samples prepared with the experimental antifungal cultures after approx. seven days of storage.

Trial 2

The freeze-dried and frozen experimental culture blends of *Propionibacterium freudenreichii* subsp. *shermanii* DSM 25846 with either *Lactobacillus paracasei* subsp. *paracasei* DSM 14514 or *Lactobacillus rhamnosus* DSM 7061 were evaluated for inhibitory activity against yeasts in yogurt. A reference sample without antifungal cultures was included for comparison. Portions of whole milk with 3.5% fat were fermented with a commercial yogurt culture. Test samples were inoculated additionally with the protective strains. After fermentation the yogurt samples were dispatched in beakers and inoculated with a pool of yeasts. The samples were stored at 6° C. and the outgrowth of the added yeast strains was monitored. FIG. 2 displays the development of the yeast pool in yogurt samples with and without antifungal cultures. An increase in yeast cell counts was observed in all samples but the reference sample without antifungal cultures showed higher yeast counts than the samples prepared with the experimental antifungal cultures after approx. seven days of storage.

The invention claimed is:

1. A method of preparing a final food or feed product, the method comprising adding to a food or feed product *Propionibacterium freudenreichii* subsp. *shermanii* DSM 25846 bacteria or a bacterial preparation comprising this bacteria.

2. A method according to claim 1, wherein said *Propionibacterium freudenreichii* subsp. *shermanii* DSM 25846 is added as a bacterial preparation also comprising a bacterium of the genus *Lactobacillus* or any other strain of the genus *Propionibacterium*, or a bacterium of the genus *Lactobacillus* and any other strain of the genus *Propionibacterium*.

3. The method according to claim 2, wherein the bacterium of *Lactobacillus* is selected from the group consisting of *Lactobacillus paracasei* subsp. *paracasei* DSM 14514, *Lactobacillus paracasei* subsp. *paracasei* DSM 25832, *Lactobacillus plantarum* DSM 25833, *Lactobacillus plantarum* DSM 25834, *Lactobacillus plantarum* DSM 25835, *Lactobacillus plantarum* DSM 25836, *Lactobacillus plantarum* DSM 25837 and *Lactobacillus rhamnosus* DSM 7061.

4. The method according to claim 2, wherein said *Propionibacterium freudenreichii* subsp. *shermanii* DSM 25846 is added as a freeze-dried bacterial preparation.

5. A method of preparing a final food or feed product, the method comprising adding to a food or feed matrix, together with a starter culture, *Propionibacterium freudenreichii* subsp. *shermanii* DSM 25846 bacteria or a bacterial preparation comprising this bacteria, in the preparation of a final food or feed product.

6. The method according to claim 5, wherein the *Propionibacterium freudenreichii* subsp. *shermanii* DSM 25846 is added as a bacterial preparation also comprising a bacterium of the genus *Lactobacillus* or any other strain of the genus *Propionibacterium*, or a bacterium of the genus *Lactobacillus* and any other strain of the genus *Propionibacterium*.

7. The method according to claim 5, wherein said *Propionibacterium freudenreichii* subsp. *shermanii* DSM 25846 is added as a freeze-dried bacterial preparation.

* * * * *